(12) United States Patent
Medeiros

(10) Patent No.: US 11,717,175 B2
(45) Date of Patent: Aug. 8, 2023

(54) WIRELESS PATIENT MONITORING SYSTEM AND METHOD WITH DISPOSABLE SENSOR ACTIVATION

(71) Applicant: GE Precision Healthcare LLC, Wauwatosa, WI (US)

(72) Inventor: Daniel W. Medeiros, Wauwatosa, WI (US)

(73) Assignee: GE Precision Healthcare LLC, Wauwatosa, WI (US)

(*) Notice: Subject to any disclaimer, the term of this patent is extended or adjusted under 35 U.S.C. 154(b) by 428 days.

(21) Appl. No.: 16/890,797

(22) Filed: Jun. 2, 2020

(65) Prior Publication Data
US 2021/0369125 A1 Dec. 2, 2021

(51) Int. Cl.
*A61B 5/0205* (2006.01)
*A61B 5/00* (2006.01)

(52) U.S. Cl.
CPC ........ *A61B 5/02055* (2013.01); *A61B 5/0022* (2013.01); *A61B 2503/045* (2013.01); *A61B 2560/0209* (2013.01); *A61B 2562/02* (2013.01)

(58) Field of Classification Search
CPC .............. A61B 5/02055; A61B 5/0022; A61B 2503/045; A61B 2560/0209; A61B 2562/02; A61B 5/01; A61B 5/0002; A61G 11/00
See application file for complete search history.

(56) References Cited

U.S. PATENT DOCUMENTS

| 8,462,734 | B2* | 6/2013 | Laine ............... H04M 1/72412 370/252 |
| 9,066,326 | B2* | 6/2015 | Narayan ............... H04W 12/06 |
| 10,057,022 | B2* | 8/2018 | Yoganathan .......... G06F 16/172 |
| 10,688,003 | B2* | 6/2020 | Underwood ............ H04L 67/12 |

(Continued)

OTHER PUBLICATIONS

NFC Forum Connection Handover Technical Specification, accessed Apr. 19, 2023, https://nfc-forum.org/build/specifications#:~:text=Connection%20Handover%20Technical%20Specification&text=Defines%20the%20structure%20and%20sequence,the%20information%20to%20be%20exchanged (Year: 2023).*

(Continued)

*Primary Examiner* — Jonathan T Kuo
(74) *Attorney, Agent, or Firm* — Andrus Intellectual Property Law, LLP

(57) ABSTRACT

A wireless patient monitoring system includes a host device configured to pair with one or more wireless physiological sensors to receive physiological data therefrom. The host device includes a nearfield communication (NFC) transmitter emitting an electromagnetic field. The system includes at least one wireless physiological sensor having a sensing element that senses physiological parameter information from a patient, a battery, and a field detection circuit configured to detect NFC field and to generate an activation signal thereupon. A sensor controller is configured to operate in a sleep state that maximizes battery power consumption by the wireless physiological sensor and to receive the activation signal from the field detection circuit when the (Continued)

NFC field is detected. After receipt of the activation signal, the sensor controller operates the wireless physiological sensor in an activated mode that enables full power consumption by the wireless physiological sensor.

18 Claims, 5 Drawing Sheets

(56) References Cited

U.S. PATENT DOCUMENTS

| | | | |
|---|---|---|---|
| 10,840,536 B2* | 11/2020 | Rogers | H01M 50/503 |
| 11,171,687 B2* | 11/2021 | Charpentier | H04B 5/0031 |
| 2012/0099566 A1* | 4/2012 | Laine | H04M 1/72412 |
| | | | 455/41.1 |
| 2014/0266776 A1* | 9/2014 | Miller | A61B 5/0015 |
| | | | 340/870.01 |
| 2014/0273820 A1* | 9/2014 | Narayan | H04W 12/06 |
| | | | 455/41.1 |
| 2015/0373831 A1* | 12/2015 | Rogers | H01M 50/502 |
| | | | 29/829 |
| 2017/0093536 A1* | 3/2017 | Yoganathan | H04W 12/068 |
| 2018/0168903 A1* | 6/2018 | Underwood | H04L 67/12 |
| 2019/0068247 A1* | 2/2019 | Hueber | G06F 1/3234 |
| 2020/0037939 A1* | 2/2020 | Castagna | G16H 40/20 |
| 2020/0195305 A1* | 6/2020 | Charpentier | H04B 5/0093 |

OTHER PUBLICATIONS

NFC Bluetooth Pairing: What is It and What Are the Benefits?, May 26, 2017, https://phiaton.com/blogs/audio/nfc-bluetooth-pairing-what-is-it-and-what-are-the-benefits (Year: 2017).*

* cited by examiner

WIRELESS PATIENT MONITORING SYSTEM AND METHOD WITH DISPOSABLE SENSOR ACTIVATION

BACKGROUND

The present disclosure relates generally to patient monitoring devices and systems for monitoring a patient's physiology and health status. More specifically, the present disclosure relates to patient monitoring devices, systems, and methods that wirelessly transmit patient physiological data.

In the field of medicine, physicians often desire to monitor multiple physiological characteristics of their patients. Oftentimes, patient monitoring involves the use of several separate monitoring devices simultaneously, such as an electrocardiograph (ECG), a pulse oximeter, a respiration monitor, a temperature monitor, etc. Several separate patient monitoring devices are often connected to a patient, tethering the patient to multiple bulky bedside devices via physical wiring or cables. Multi-parameter monitors are also available where different sensor sets may be connected to a single monitor. However, such multi-parameter systems may be even more restrictive than separate monitoring devices because they require all of the sensors attached to a patient to be physically attached to a single monitor, resulting in multiple wires running across the patient's body. Thus, currently available patient monitoring devices often inhibit patient movement, requiring a patient to stay in one location or to transport a large monitor with them when they move from one place to another.

Further, currently available monitoring devices are often power intensive and either require being plugged into a wall outlet or require large battery units that have to be replaced and recharged every few hours. Thus, monitoring multiple patient parameters is power intensive and battery replacement is costly in labor and parts. Thus, frequent monitoring is often avoided in order to limit cost and patient discomfort, and instead patient parameters are infrequently spot checked, such as by periodic nurse visits one or a few times a day. However, patients that are not being regularly monitored may encounter risky health situations that that go undetected for a period of time, such as where rapid changes occur in physiological parameters that are not checked by a clinician until hours later or until a critical situation occurs. Thus, it is often desirable to continually or frequently obtain certain physiological information from a patient, which is a battery-intensive endeavor.

SUMMARY

This Summary is provided to introduce a selection of concepts that are further described below in the Detailed Description. This Summary is not intended to identify key or essential features of the claimed subject matter, nor is it intended to be used as an aid in limiting the scope of the claimed subject matter.

In one embodiment, a wireless patient monitoring system includes a host device configured to pair with one or more wireless physiological sensors to receive physiological data therefrom. The host device includes a nearfield communication (NFC) transmitter emitting an electromagnetic field. The system includes at least one wireless physiological sensor having a sensing element that senses physiological parameter information from a patient, a battery, and a field detection circuit configured to detect the electromagnetic field emitted by the NFC transmitter and to generate an activation signal upon detection of the NFC field. A sensor controller is configured to operate in a sleep state that maximizes battery power consumption by the wireless physiological sensor and to receive the activation signal from the field detection circuit when the electromagnetic field emitted by the NFC transmitter is detected. After receipt of the activation signal, the sensor controller operates the wireless physiological sensor in an activated mode that enables full power consumption by the wireless physiological sensor.

One embodiment of a method of controlling a wireless physiological sensor includes operating the wireless physiological sensor in a sleep state that minimizes battery power consumption by the wireless physiological sensor, and then detecting, with a field detection circuit, an electromagnetic field emitted by an NFC transmitter. Upon detecting the NFC field, an activation signal is generated to a sensor controller in the wireless physiological sensor. Only after receipt of the activation signal, the sensor controller is then operated in an activated mode where processing of physiological parameter information received from the sensing element and generation of physiological data, and/or other physiological sensor functionality such as pairing with a host device and transmission of the physiological data thereto, is enabled.

Various other features, objects, and advantages of the invention will be made apparent from the following description taken together with the drawings.

BRIEF DESCRIPTION OF THE DRAWINGS

The present disclosure is described with reference to the following Figures.

DETAILED DESCRIPTION

Figure 1:
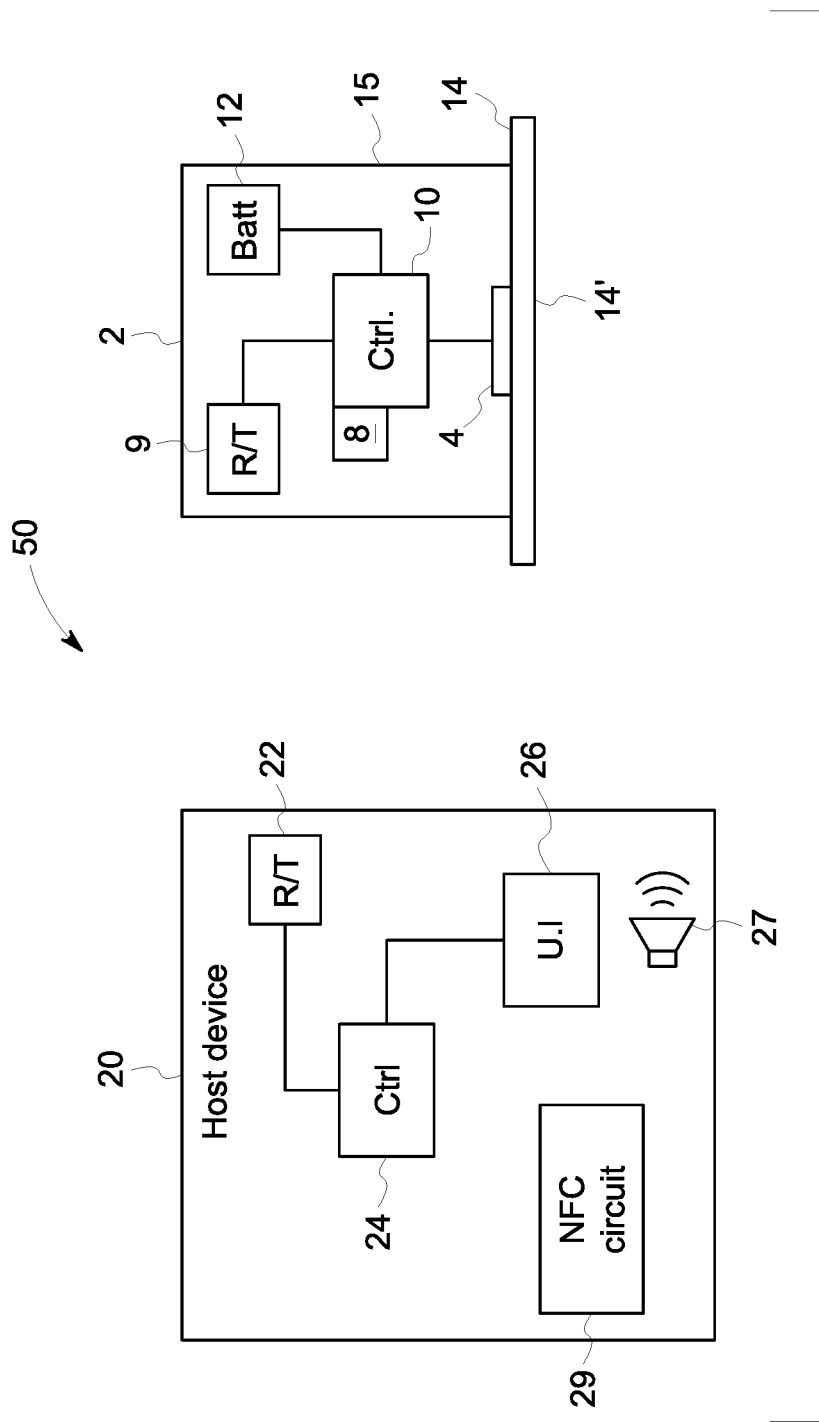
FIG. 1 is a schematic diagram of a wireless patient monitoring system according to one embodiment of the present disclosure.

The present inventor has recognized that wireless monitoring systems are desirable, for example to provide more comfort and mobility to the patient being monitored. The patient's movement is not inhibited by wires between sensor devices and/or computing devices that collect and process the physiological data from the patient. Thus, small sensing devices and sensors that can be easily attached to the patient's body are desirable, such as sensing devices that are wearable portable computing devices. In order to do so, the size of the wireless sensing devices must be small. The present inventor has recognized that an important aspect of decreasing the size and weight of wireless physiological sensors is decreasing battery size. This is especially important and challenging for developing wireless sensors for monitoring neonates, where size and weight requirements are lower to accommodate the small body size of a neonate. Preferably neonatal wireless physiological sensors are small enough to be utilized on premature neonates, including to monitor physiological parameters on neonates weighing less than 1 pound. For such applications, sensor weight becomes very restrictive. The inventor has recognized that sensors for such neonatal applications need to be very light, such as having a maximum weight of 5-10 grams.

In view of the foregoing problems and challenges in the relevant art, the inventor has developed a disposable sensor with a non-rechargeable battery to minimize battery size and weight of battery-related components. However, the inventor has recognized that use of a non-rechargeable battery poses additional issues relating to shelf-life of the wireless sensor. All batteries slowly discharge when not in use. The inventor has recognized that a wireless physiological sensor needs to have adequate shelf life after manufacture that can account for distribution and shipping to an end customer, and also for storage by the customer until needed on a patient. Accordingly, the inventor developed the disclosed system and method of sensor operation whereby the wireless physiological sensor is operated in a sleep state where minimal battery power is consumed by the physiological sensor until such time as the sensor is needed for monitoring a patient.

The disclosed system and method are configured to take advantage of existing near field communication (NFC) systems in patient monitoring devices and other patient care devices, including in infant care devices such as incubators or warmers, to trigger an activation process that brings the sensor out of the sleep state and causes the sensor to begin executing a pairing routine so that it can pair with the host device and transmit monitoring data thereto. Namely, the inventor has recognized that the electromagnetic field emitted by an NFC transmitter (the "NFC field") already operating in host devices can be detected with NFC field detection circuitry that consumes very little battery power. Thus, NFC field detection can be implemented as a low-power way to detect proximity of the sensor to the host device. The assumption is that when the wireless sensor is placed in proximity to the host device, it is being prepared and intended for use and thus should be activated, or woken from the sleep state. Though the sensor may not communicate via NFC, an antenna tuned to detect an NFC field frequency (i.e., 13.56 MHz) can be easily installed and NFC field detection performed without incorporating full NFC functionality into the wireless physiological sensor. However, in some embodiments the wireless sensor may include an NFC tag and be capable of communicating with the host via NFC.

The controller in the wireless sensor is configured to initially operate in a sleep state to minimize battery consumption. The disclosed wireless physiological sensor includes an antenna configured to detect the electromagnetic field emitted by the NFC transmitter on a host device, e.g., a patient monitor, infant care device, etc. The antenna is connected to an NFC detector circuit, such as a comparator configured to generate a positive output when the NFC field is detected, or an NFC peripheral configured to generate an activation signal when the NFC field is detected.

In the sleep state only predefined circuitry is active, such as only circuitry configured to detect an activation input when the NFC field is picked up by the antenna. Thereby, power consumption of the wireless sensor is reduced and battery life and shelf life of the sensor are extended. For instance, in the sleep mode only one IO pin configured to receive the activation signal as input may be active. For example, a rising edge detector may be configured to detect a non-zero input at the IO pin connected to the NFC field detector, and may thereby initiate the activation mode once the activation input is received.

FIG. 1 depicts one embodiment of a wireless patient monitoring system 50 configured to monitor one or more physiological parameters of a patient. The patient monitoring system 50 includes a wireless physiological sensor 2, which is preferably a disposable sensor configured for a single use, and a host device, such as a patient monitor. The wireless physiological sensor has a sensing element 4 arranged on a substrate 14. The sensor controller 10 receives physiological information detected by the sensing element 4. The sensing element 4 may be any type of device for sensing or detecting physiological information from the patient, which may include but is not limited to a skin electrode, temperature sensor, pressure sensor, flow sensor, infrared or other pulse oximetry sensor, or the like. For instance, the monitored parameter value may be heart rate, respiration rate, SpO2, or temperature.

The sensor controller 10 is configured to receive and process the physiological information from the sensing element 4, such as to filter and digitize the information, as well as to process the digital signal to extract relevant physiological values therefrom. The sensor controller 10 may include a processor as well as signal processing elements, including filters, amplifiers, or the like as is required or appropriate for processing the type of physiological information that the sensing element 4 is configured to detect. In certain types of physiological sensors 2, the sensor controller 10 may be configured to determine a discrete value based on the physiological parameter information received from the sensing element 4, such as a heart rate, respiration rate, SpO2, temperature, etc.

A wireless transmitter 9 or transceiver communicates the recorded physiological parameter values and other information to a host device 20, such as a patient monitor or other device configured to receive the physiological measurements. The transmitter 9 is configured to communicate the physiological information to the host device 20 by a wireless communication means, which may include any appropriate wireless communication protocol. In one embodiment, the host device 20 is also configured to communicate information to the sensor, and thus is configured with a transceiver 22 that communicates with a transceiver 9 in the physiological sensor 2. In one embodiment, the transceiver 22 is configured as a body area network with one or more transceivers 9 in one or more physiological sensors 2 on the patient. In other embodiments, the physiological sensor 2 and host device 20 may communicate by other radio protocols, such as but not limited to Bluetooth, Bluetooth Low Energy (BLE), ANT, and Zigbee.

In various embodiments, the host device 20 may be a standalone patient monitor or may device incorporated into a larger patient care system, such as an incubator or warmer, or a multi-parameter patient monitor receiving physiological information from multiple different types of sensing devices. The host device 20 may include a host controller 24, which may be configured to process and/or display physiological data recorded by the sensor 2. The host device 20 may include a user interface 26, such as for displaying the physiological information recorded by the sensor 2. The user interface may include a display device and may also include one or more speakers 27 or buzzers for generating an audio alert.

The wireless physiological sensor 2 shown in FIG. 1 includes a sensor module 15 mounted on the substrate 14 and housing the sensor controller 10, transmitter 9 (which may be a transceiver), and a battery 12 to power the wireless sensor. The battery is non-rechargeable, which cuts down on the weight of the wireless sensor 2 by eliminating components necessary for battery charging. The sensor module 15 may comprise a housing that is attached to the substrate 14 and configured to house and protect the various components of the sensor 2.

Figure 2A:
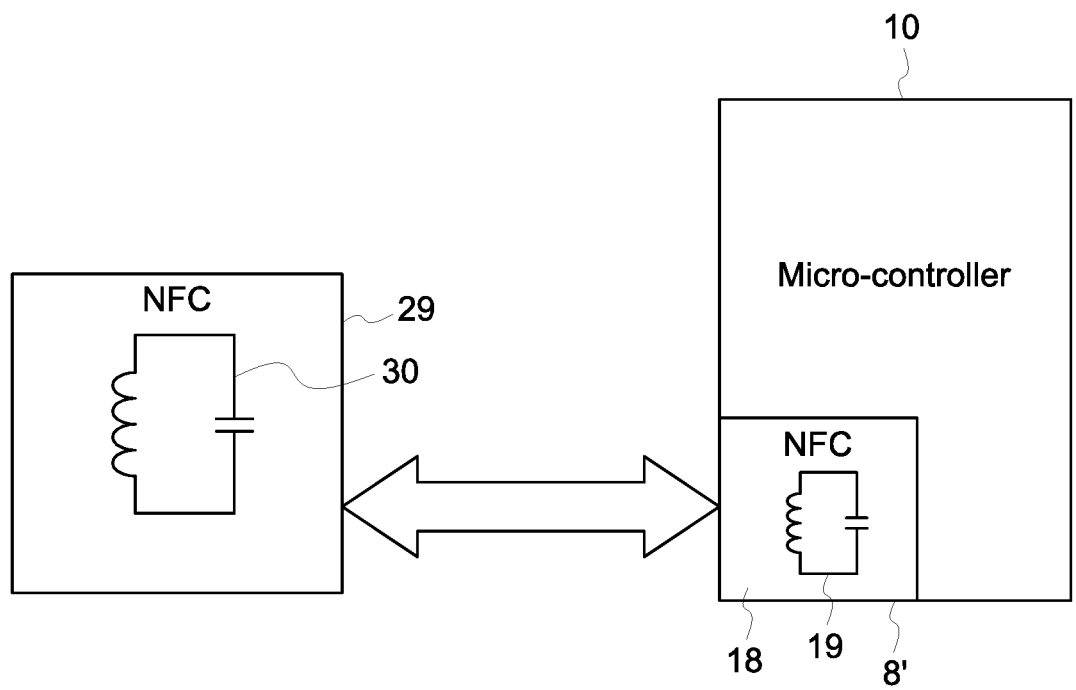
FIGS. 2A and 2B schematically depict embodiments of an NFC transmitter and an NFC field detector comprising an antenna tuned to detect an NFC field.
Figure 2B:
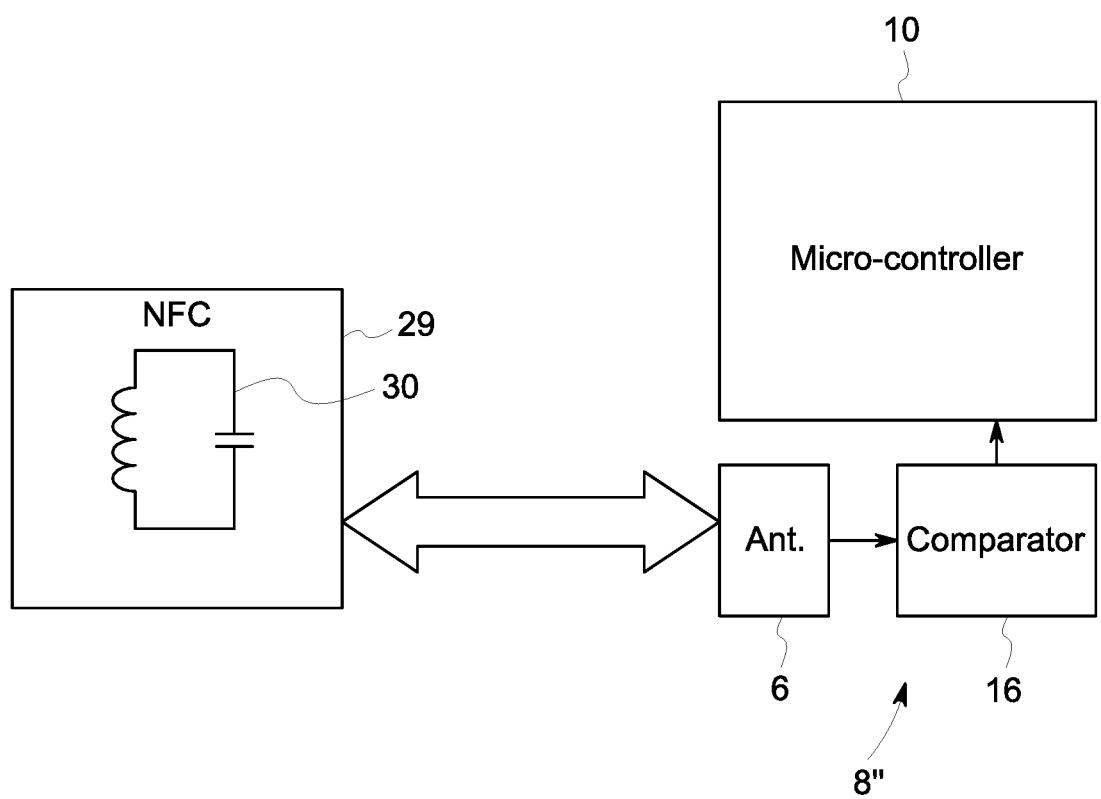

With reference also to FIGS. 2A and 2B, the host device 20 includes an NFC circuit 29 comprising an NFC antenna 30 and other standard NFC circuit components. The NFC circuit 29 is configured to transmit RF energy in accordance with NFC standards, which are well known. That RF energy is radiated in an electromagnetic field by the antenna 30. That NFC field is detected by an NFC detection circuit 8 in the wireless physiological sensor 2. The NFC detection circuit 8 includes an antenna 6 connected to circuitry configured to generate the activation signal when an NFC field is picked up by the antenna 6. As described above, the antenna 6 is tuned to resonate at the designated NFC frequency. Thereby, the antenna 6 will pick up the NFC field once the wireless sensor 2 comes within range of the NFC circuit 29 in the host device.

The NFC detection circuit 8 includes circuit elements configured to generate an activation signal when the antenna picks up the NFC field. In FIG. 2A, the NFC detection circuit 8' is an NFC peripheral 18. The NFC peripheral 18 may be integrated into the sensor controller 10 and includes an NFC antenna 19. In such an embodiment, the wireless physiological sensor 2 may be configured to communicate with the host device 20 via NFC.

FIG. 2B depicts another embodiment in which the sensor 2 is not configured for NFC communication and only for NFC field detection. In this embodiment, the NFC detection circuit 8" includes an antenna 6 tuned to the NFC frequency, but does not include other NFC circuitry elements. Instead, a comparator 16 is provided between the antenna 6 and the sensor controller 10. The comparator 16 has two analog inputs, one being the antenna 6 and the other being a reference equivalent to the voltage provided by the antenna when a NFC field is in proximity. The comparator 16 compares the inputs and provides a binary digital output based thereon, where the output indicates whether or not the NFC field is detected by the antenna. The output of the comparator 16 serves as the activation signal.

Figure 3:
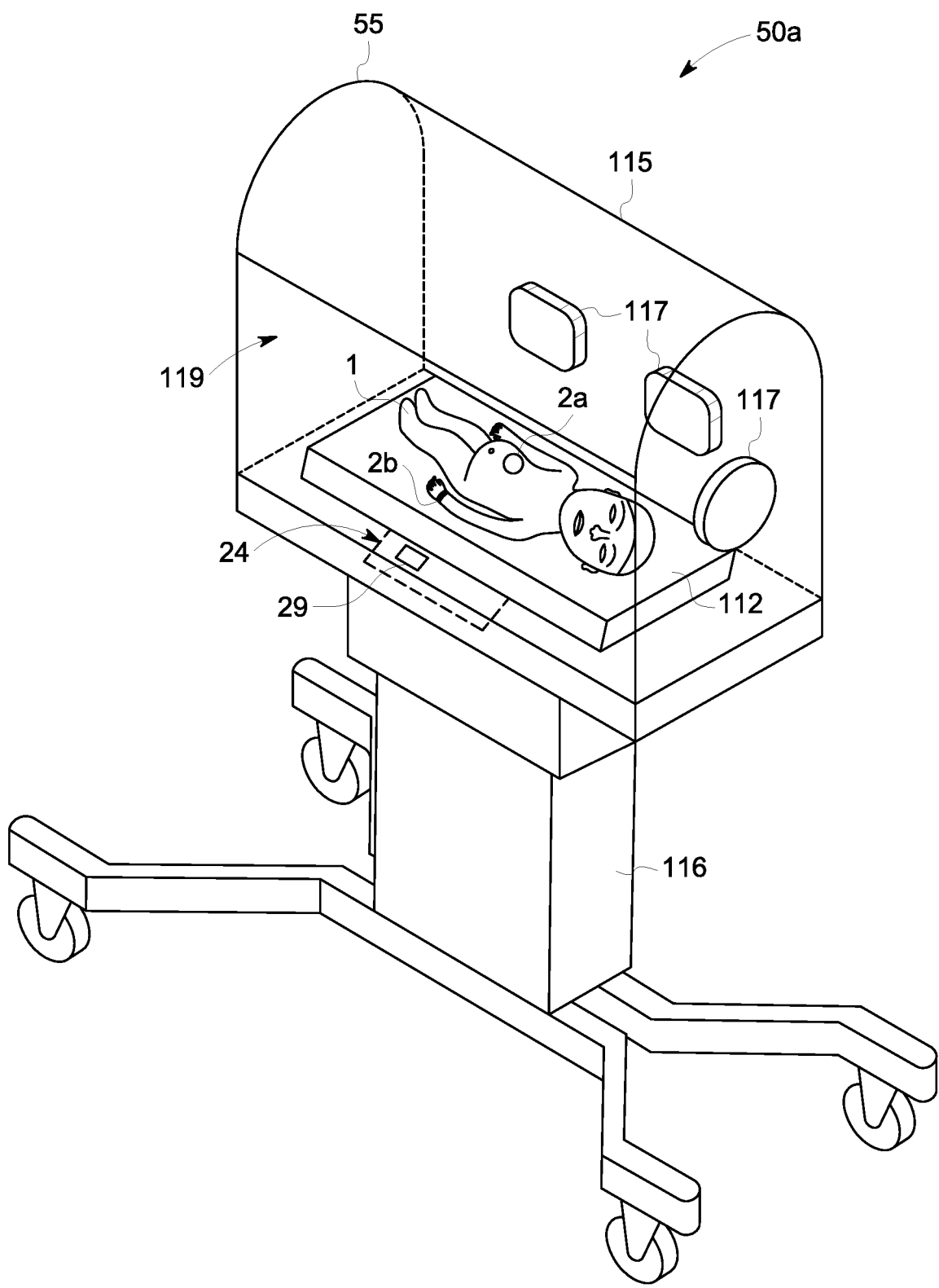
FIG. 3 depict a wireless patient monitoring system in an infant care device according to another embodiment of the present disclosure.

Maintaining appropriate body temperature of a neonate, particularly a premature neonate housed in an incubator or warmer, relies on accurate temperature measurements from the neonate. FIG. 3 depicts an exemplary temperature monitoring system 50a for a neonate comprising two wireless temperature sensors 2a and 2b attached to the neonate to determine neonatal temperature. The first temperature sensor 2a senses a body temperature of the neonate and the second temperature sensor 2b senses a peripheral temperature. The temperature sensors 2a and 2b are disposable temperature sensors configured as described herein to detect the infant care device, here an incubator 55, configured to monitor and maintain an appropriate environment for the neonate 1. The incubator 55, which in other embodiments could be an infant warmer such as a radiant warmer, has a heater system providing a heated environment for the infant 1. Here, the incubator 55 is the host device and contains an NFC circuit 29 that emits an NFC field. The temperature sensors 2a and 2b each have field detection circuits 8 configured to detect that NFC field when the sensor 2a, 2b is in close proximity to the NFC circuit 29. Pairing between each temperature sensor 2a, 2b and the host controller 24 of the incubator host device 55 is then executed. Once pairing occurs, the temperature of the microenvironment 119 maintained in the incubator 55 can be controlled based on the infant's temperature.

In the exemplary incubator system of FIG. 3, the incubator system 55 includes a platform 112 supporting the infant 1. A canopy 115 is provided over the platform 112 to form a microenvironmental chamber 119 providing a controlled environment isolated from the surrounding environment. The canopy 115 has access portals 117 to facilitate access to the infant 1 without significantly altering the microenvironment within the chamber 119. The canopy 115 is supported on a support structure 116, or frame, that houses and supports control systems for controlling aspects of the microenvironment within the chamber 119, including a heater system, as well as other systems for controlling humidity, airflow, etc. within the chamber 119. The controller 24 includes software that processes the measurements from the respective temperature probes 2a, 2b to control various aspects of the system.

In the examples, the system 50 includes a body temperature probe 2a removably fixed to the infant's torso, such as to the infant's abdomen, to measure a body temperature of the infant 1, and includes a peripheral temperature probe 2b removably fixed to the infant's extremity to measure a peripheral temperature of the infant 1. Each temperature probe 2a, 2b has a respective temperature sensing element thermally contacting and detecting a temperature at a particular location on the infant's skin. In the particular embodiment, the body temperature probe 2a comprises an adhesive connection on the bottom side 14' of the substrate 14 adhering the wireless body temperature sensor 2a to the skin of an infant's torso, such as above the infant's liver. In the depicted embodiment, the peripheral temperature probe 2b has a fixation band fixing the peripheral temperature sensor 2b to the infant's hand.

Figure 4:
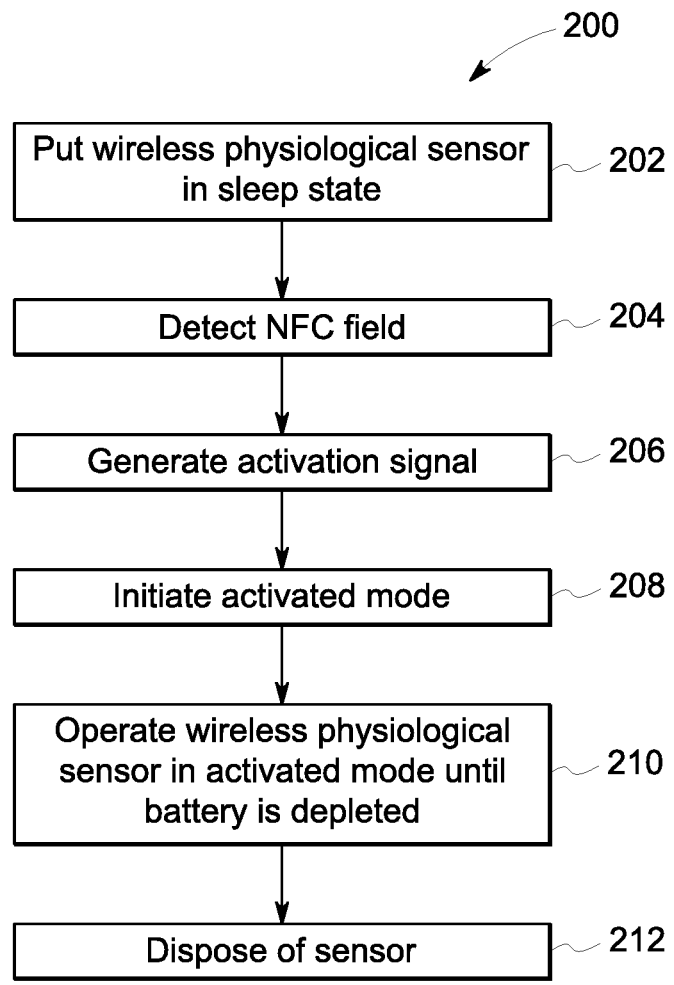
FIGS. 4-5 depict methods of controlling a wireless physiological sensor according to embodiments of the present disclosure.
Figure 5:
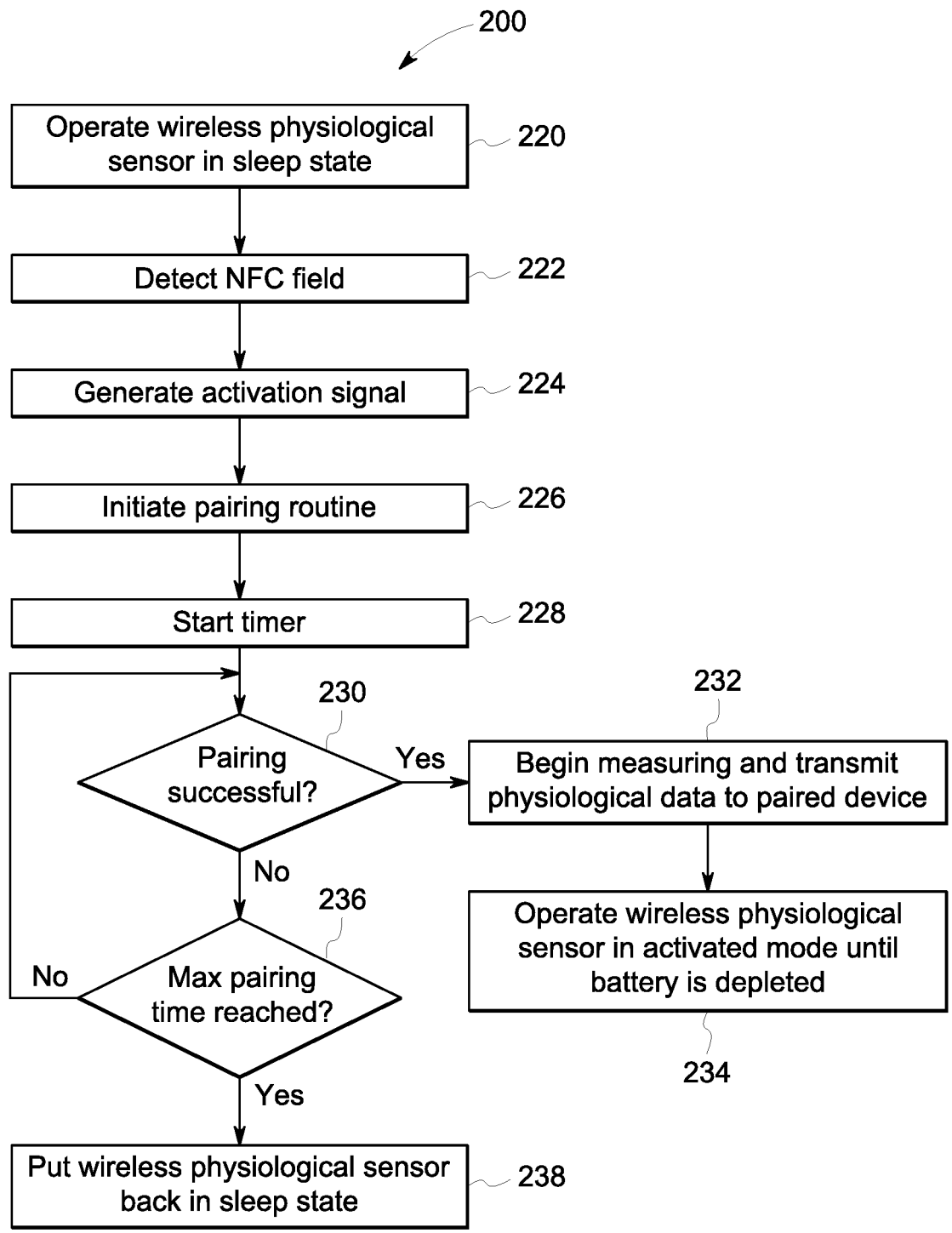

FIGS. 4 and 5 depict exemplary methods 200 of operating wireless physiological sensors 2 in accordance with the present disclosure. In FIG. 4, the method 200 includes placing the wireless physiological sensor 2 in a sleep state at step 202. For example, the sleep state may be where the sensor controller 10 is inactive except for the field detection circuit 8 and any other circuitry necessary to detect the activation signal. In the sleep state, minimal battery power is consumed by the wireless physiological sensor 2, thereby maximizing the shelf life of the disposable sensor having a non-rechargeable battery. Once an NFC field is detected by the field detection circuit 8, step 204, the activation signal is generated at step 206. Examples of activation signal generation means and logic are described above, which for example may be by an NFC peripheral 18 or by a comparator 16.

The activated mode is initiated at step 208 to bring the wireless physiological sensor out of the sleep state and begin pairing and physiological sensing operations. In the activated mode, full power consumption by the wireless physiological sensor is enabled. For example, all of the various elements within the physiological sensor 2 are powered, such as the sensing element 4 (if it is a powered device), the transceiver 9, and any other powered element within the wireless physiological sensor 2. In certain embodiments, once fully activated, the wireless physiological sensor 2 may remain in the activated mode until the battery is depleted, as represented at step 210. After batter depletion, the sensor is disposed, as represented at step 212.

FIG. 5 depicts another embodiment of a method 200 of operating a wireless physiological sensor 2. The wireless physiological sensor is operated in a sleep state, represented at step 220. Once an NFC field is detected at step 222, an activation signal is generated at step 224. Instructions are then executed, such as by the sensor controller 10, to initiate a pairing routine at step 226. For example, the wireless physiological sensor 2 will make itself discoverable by a host device 20 within range. Various protocols may be utilized for pairing. In some preferred embodiments, NFC is not used for pairing. For example, Bluetooth may be used for purposes of pairing, and initiating the pairing routine may include transmitting advertising packets from the sensor 2 according to Bluetooth protocol.

In some embodiments, the sensor controller 10 may be configured such that it attempts to pair for a predetermined amount of time after initial activation and, if pairing is not successful, to return to the sleep state. Such a configuration will account for errant activations by NFC devices other than a host device 20. For example, the wireless physiological sensor 2 may come within range of an NFC transmitter during shipping or during inventory or storage processes, such as NFC utilized for identification of shipping/storage containers, etc. The wireless physiological sensor 2 may thus be configured to attempt pairing for a short amount of time after receiving an activation signal so that significant battery powers is not wasted by pairing attempts when pairing is not possible or intended. Thus, the sensor controller may be configured to execute a process upon activation that avoids permanent activation and draining the battery when activation was not intended and the sensor will not be put into immediate use.

In the example at FIG. 5, a timer is be started at step 228 once the activation signal is received and pairing is being initiated. If pairing is successful at step 230, then the sensor will continue in the activated mode and begin measuring and transmitting physiological data to the paired device, as represented at step 232. The wireless physiological sensor will be operated in the activated mode until the battery is depleted, as represented at step 234. If, on the other hand, pairing is not successful at step 230, analysis is conducted to determine when a predetermined maximum pairing time has been reached. This may be a relatively short amount of time, such as 30 seconds or one minute, or could be longer depending on the monitoring application and number of sensors that will need to be paired, etc. Once the maximum pairing time has been reached at step 236 and pairing has not been successful, then the wireless physiological sensor will be put back into the sleep state at step 238 so that the battery usage can be minimized when the wireless physiological sensor is not in use and the sensor shelf life extended as much as possible.

This written description uses examples to disclose the invention, including the best mode, and also to enable any person skilled in the art to make and use the invention. Certain terms have been used for brevity, clarity and understanding. No unnecessary limitations are to be inferred therefrom beyond the requirement of the prior art because such terms are used for descriptive purposes only and are intended to be broadly construed. The patentable scope of the invention is defined by the claims, and may include other examples that occur to those skilled in the art. Such other examples are intended to be within the scope of the claims if they have features or structural elements that do not differ from the literal language of the claims, or if they include equivalent features or structural elements with insubstantial differences from the literal languages of the claims.

I claim:
1. A wireless patient monitoring system comprising:
a host device configured to pair with one or more wireless physiological sensors to receive physiological data therefrom, the host device comprising a near field communication (NFC) transmitter emitting an electromagnetic field;
at least one wireless physiological sensor including:
a sensing element that senses physiological parameter information from a patient;
a battery;
a field detection circuit configured to detect the electromagnetic field emitted by the NFC transmitter and to generate an activation signal upon detection;
a sensor controller configured to:
operate in a sleep state that minimizes battery power consumption by the wireless physiological sensor;
receive the activation signal from the field detection circuit when the electromagnetic field emitted by the NFC transmitter is detected;
start a timer upon receipt of the activation signal;
execute a pairing routine;
if pairing is not successful within a predetermined time, then return to the sleep state;
if pairing is successful within the predetermined time, operate in an activated mode that enables full power consumption by the wireless physiological sensor.

2. The system of claim 1, wherein the field detection circuit includes an antenna and a comparator, wherein the comparator is configured to transmit the activation signal to the sensor controller upon detection by the antenna of the electromagnetic field emitted by the NFC transmitter.

3. The system of claim 1, wherein the field detection circuit includes an NFC peripheral configured to transmit the activation signal to the sensor controller upon detection of the electromagnetic field emitted by the NFC transmitter.

4. The system of claim 1, wherein the sensor controller is further configured such that, once the pairing is successful, the wireless physiological sensor is permanently operated in the activated mode until the battery is depleted such that return to the sleep state is not permitted.

5. The system of claim 1, wherein the wireless physiological sensor further includes a sensor transceiver configured to communicate with a host transceiver on the host device to facilitate pairing, wherein communication between the sensor transceiver and the host transceiver is by a communication protocol other than NFC.

6. The system of claim 1, wherein the battery is not rechargeable and the wireless physiological sensor is configured to be disposed after the battery is depleted.

7. The system of claim 1, wherein in the sensor controller is configured such that in the sleep state the sensor controller is inactive except for the field detection circuit.

8. The system of claim 7, wherein the field detection circuit includes a rising edge detector in the sensor controller to detect the activation signal.

9. The system of claim 1, wherein the sensor controller is further configured such that, only in the activated mode, it processes the physiological parameter information received from the sensing element to generate physiological data.

10. The system of claim 1, wherein the physiological data includes one of a temperature value, a heart rate value, a respiration rate value, or an SpO$_2$ value.

11. The system of claim 1, wherein the host device is a patient monitor and wireless physiological sensor is at least one of a temperature sensor, an ECG sensor, an SpO$_2$ sensor, or a respiration sensor.

12. The system of claim 1, wherein the host device is an infant care device and the sensor is a wireless temperature sensor configured to attach to a neonate housed in the infant care device, wherein the infant care device further comprises a heater and is configured to control the heater based on a temperature transmitted by the wireless temperature sensor.

13. A method of operating a wireless physiological sensor, the method comprising:

operating the wireless physiological sensor in a sleep state that minimizes battery power consumption by the wireless physiological sensor;

detecting, with a field detection circuit within the wireless physiological sensor, an electromagnetic field emitted by an NFC transmitter;

generating an activation signal to a sensor controller in the wireless physiological sensor when the electromagnetic field emitted by the NFC transmitter is detected; and starting a timer upon receipt of the activation signal;

executing a pairing routine to pair with a host device;

if pairing is not successful within a predetermined time, then returning to the sleep state; and if pairing is successful within the predetermined time, operating the sensor controller in an activated mode to enable processing of physiological parameter information received from a sensing element to generate physiological data.

14. The method of claim 13, wherein detecting the electromagnetic field emitted by the NFC transmitter is detected includes operating a comparator to generate the activation signal to the sensor controller when the electromagnetic field emitted by the NFC transmitter is detected.

15. The method of claim 13, further comprising, once pairing is successful, permanently operating the wireless physiological sensor in the activated mode until the battery is depleted such that return to the sleep state is not permitted.

16. The method of claim 13, further comprising, only after receipt of the activation signal and pairing is successful, processing information from a sensing element on the physiological sensor.

17. The method of claim 13, wherein the physiological data includes one of a temperature value, a heart rate value, a respiration rate value, or an $SpO_2$ value.

18. The method of claim 13, wherein in the sleep state the sensor controller is inactive except for the field detection circuit.

* * * * *